(12) United States Patent
Mueller

(10) Patent No.: US 10,675,148 B2
(45) Date of Patent: Jun. 9, 2020

(54) INTRAOCULAR LENS CARTRIDGE HAVING A LUBRICANT FEED DUCT AND INJECTOR INCORPORATING SAID CARTRIDGE

(71) Applicant: Carl Zeiss Meditec AG, Jena (DE)

(72) Inventor: Marco Mueller, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 231 days.

(21) Appl. No.: 15/996,273

(22) Filed: Jun. 1, 2018

(65) Prior Publication Data

US 2018/0271647 A1 Sep. 27, 2018

Related U.S. Application Data

(63) Continuation of application No. PCT/EP2016/078944, filed on Nov. 28, 2016.

(30) Foreign Application Priority Data

Dec. 3, 2015 (DE) .......................... 10 2015 224 141

(51) Int. Cl.
*A61F 2/16* (2006.01)

(52) U.S. Cl.
CPC .......... *A61F 2/1678* (2013.01); *A61F 2/1675* (2013.01)

(58) Field of Classification Search
CPC ...... A61F 2/167; A61F 2/1691; A61F 2/1678; A61F 2/16; A61F 2/1662

(Continued)

(56) References Cited

U.S. PATENT DOCUMENTS 5,944,725 A 8/1999 Cicenas et al.
6,491,697 B1 12/2002 Clark et al.
(Continued)

FOREIGN PATENT DOCUMENTS

CN 1602817 A 4/2005
EP 1 808 150 A1 7/2007
(Continued)

OTHER PUBLICATIONS

Translation of Search Report of the National Intellectual Property Administration of China dated Jul. 28, 2019 in corresponding Chinese application 201680070646.4.
(Continued)

*Primary Examiner* — George J Ulsh
(74) *Attorney, Agent, or Firm* — Walter Ottesen, P.A.

(57) ABSTRACT

A cartridge accommodates an intraocular lens and includes first and second cartridge parts pivotally moveable relative to each other to define an open state and a closed state. The first cartridge part has a first base element and a first plate-like wing extending from the first base element. The second cartridge part has a second base element and a second plate-like wing extending from the second base element. The first and second base elements conjointly define a receiving chamber for the lens when the first and second cartridge parts are in the closed state. A lubricant feed arrangement supplies a lubricant for the lens into the receiving chamber from outside of the cartridge when the cartridge is in the closed state. The lubricant feed arrangement includes a feed channel which is formed in one of the cartridge parts and opens into the receiving chamber.

10 Claims, 9 Drawing Sheets

(58) Field of Classification Search
USPC .......................................................... 606/107
See application file for complete search history.

(56) References Cited

U.S. PATENT DOCUMENTS

| | | | |
|---|---|---|---|
| 8,109,938 B2 | 2/2012 | Pessin | |
| 8,123,804 B2 | 2/2012 | Tanaka | |
| 8,470,031 B2 | 6/2013 | Pankin et al. | |
| 2004/0199174 A1 | 10/2004 | Herberger et al. | |
| 2007/0168026 A1 | 7/2007 | Nagasaka | |
| 2010/0130985 A1* | 5/2010 | Tanaka | A61F 2/1678 606/107 |
| 2016/0250069 A1 | 9/2016 | Dockhorn et al. | |

FOREIGN PATENT DOCUMENTS

| | | |
|---|---|---|
| EP | 1905386 A1 | 4/2008 |
| FR | 2820633 A1 | 8/2002 |
| FR | 2892920 A1 | 5/2007 |
| WO | 2013/038689 A1 | 3/2013 |
| WO | 2013/168410 A1 | 11/2013 |
| WO | 2014/208507 A1 | 12/2014 |

OTHER PUBLICATIONS

Translation of the first Office action of the National Intellectual Property Administration of China dated Aug. 2, 2019 in corresponding Chinese application 201680070646.4.
International Search Report dated Feb. 2, 2017 of international application PCT/EP2016/078944 on which this application is based.
English translation of the Office action of the German Patent Office dated Aug. 31, 2016 of German patent application 10 2015 224 141.6 on which the claim of priority is based.

* cited by examiner

INTRAOCULAR LENS CARTRIDGE HAVING A LUBRICANT FEED DUCT AND INJECTOR INCORPORATING SAID CARTRIDGE

CROSS REFERENCE TO RELATED APPLICATIONS

This application is a continuation application of international patent application PCT/EP2016/078944, filed Nov. 28, 2016, designating the United States and claiming priority from German application 10 2015 224 141.6, filed Dec. 3, 2015, and the entire content of both applications is incorporated herein by reference.

FIELD OF THE INVENTION

The invention relates to a cartridge for receiving an intraocular lens for an injector, and to an injector having such a cartridge for introducing the intraocular lens into an eye.

BACKGROUND OF THE INVENTION

It is known that viscoelastic materials or fluids, which are also referred to as OVDs (ophthalmo-viscosurgical devices), are widely used in operative ophthalmology. In cataract operations, in which an eye lens is fragmented and aspirated and then an intraocular lens is inserted, these materials are used. During the surgical procedure, they are also injected into the eye. As a result, for example, inter alia, the stability of the anterior eye chamber is maintained. Furthermore, the material of the intraocular lens is protected by these materials, and the endothelium of the cornea is likewise protected. Furthermore, in this surgical procedure, volume is provided in the eye as a result, in order for it to be possible to remove tissue precisely and reliably.

However, once the surgical procedure has been completed, these auxiliary surgical fluids have to be removed completely from the eye again, since, if they remain in the eye, complications can arise and in particular the eye pressure can also increase undesirably.

U.S. Pat. No. 8,123,804 B2 discloses a cartridge for an intraocular lens, which has a plate-like cover arranged in a pivotable manner on a well-like part of the cartridge, the cover closing the volume of the well-like part. The cover and the well-like part form the cartridge. The intraocular lens is accommodated in the volume before it is pushed out and implanted in the eye with an injector. This cover has a hole which leads to the outside and through which, in the closed state of the cartridge, a lubricant can be introduced into the volume.

A significant drawback is that, on account of the rectilinear hole, which is small and thus not very deep along the hole axis, when the lubricant is introduced, the intraocular lens can also be damaged. The introduction normally takes place using a syringe with a needle, which is introduced into the hole. In the process, the needle can easily be introduced too far and come into contact with the intraocular lens with the result that the latter can be scratched and/or shifted. Shifting then also results in the local subsequent folding of the intraocular lens in the injector tip no longer taking place as it should during the pushing-out operation, since the starting position before folding has been changed. This can cause problems during introduction into the eye. Furthermore, in this prior art, the cartridge is formed with its cover and well-like part such that folding of the intraocular lens is made possible only in the injector tip adjoining the cartridge, and so the closing of the plate-like cover of the cartridge has no effect whatsoever on the orientation and shape of the intraocular lens in the volume.

Furthermore, US2007/0168026 discloses a cartridge for an intraocular lens, which has two parts which are pivotable relative to one another and form a receiving area for the intraocular lens in the closed state. In a rear area of the parts, and thus next to a hinge that connects the parts in a pivotable manner, a hole for introducing a lubricant is formed. In this embodiment, the problem arises that the introduction of the lubricant impedes the folding of the lens. As a result, the desired folding direction of the lens toward the hinge is significantly impaired and inhibited, such that the folded end position of the intraocular lens in the cartridge is not achieved or achieved only inadequately, this in turn being disadvantageous for the further pushing-out operation and resulting in damage to the lens or an undesired pushing-out position at the front end of the injector tip.

US2016/0250069 discloses a device for receiving an intraocular lens. In this document, a cartridge is shown which has two half-shells that are connected directly together in a pivotable manner, a wing also being formed on each of the half-shells. Between the half-shells there extends a cover, which has a cutout, through which a lubricant is feedable into a chamber in which the intraocular lens is arranged. However, the feed can take place only in the open state of the wings and thus also of the half-shells. As a result, the cover, which is fastened only on one side to only one half-shell by way of a film hinge, can be lifted and the lubricant can undesirably escape from the chamber. Furthermore, the cutout in the cover is hard to locate, and so the needle of a lubricant feed unit can also slip off. Moreover, the cutout is geometrically disadvantageous since the needle of the lubricant feed unit can be passed easily therethrough and can then damage the intraocular lens.

In US2004/0199174, a device for folding an intraocular lens and a storage system for an intraocular lens are described.

SUMMARY OF THE INVENTION

It is an object of the present invention to provide a cartridge for an intraocular lens which, in the closed state of the cartridge, allows a reliable external feed of the lubricant and reduces the risk of damage to the intraocular lens. A further object is to provide an injector having such a cartridge.

A cartridge according to the invention is configured to receive an intraocular lens. It is therefore an intraocular-lens receiving cartridge. The cartridge is configured for an injector for introducing the intraocular lens into an eye. The cartridge has two cartridge parts that are pivotable relative to one another about a longitudinal axis of the cartridge. Here, one cartridge part has a channel-like base element and a plate-like wing adjoining the latter. A further cartridge part likewise has a channel-like base element and a plate-like wing adjoining the latter. The cartridge parts are each formed in particular integrally. In the closed state of the cartridge, at least a part of an in particular tubular receiving chamber for the intraocular lens, and thus an intraocular-lens receiving chamber, is formed by the base elements. As regards their channel-like configuration, the base elements are thus formed as bulbous shell parts which are thus elements that are curved in particular in opposite directions to one another and are optionally arcuate. The cartridge furthermore has a lubricant feed device with which, for the intraocular lens, with the cartridge closed, and then also from outside the cartridge, a fluid lubricant is feedable preferably radially into the receiving chamber.

An essential concept of the invention is that the lubricant feed device has a first feed duct which is formed in at least one cartridge part and leads into the receiving chamber. As a result of such a configuration of the cartridge, it is possible, even in the closed state of this cartridge and thus with the cartridge parts joined together or pivoted toward one another, or moved together, to the maximum extent, for lubricant nevertheless to be introduced radially through one of the cartridge parts. Therefore, lubricant no longer has to be fed from an end that is open at the front or an end that is open at the rear, as seen in the direction of the longitudinal axis of the cartridge. Rather, it is now possible, with the cartridge according to the invention, to feed lubricant from outside the cartridge at an angle other than 0° and 180° to the longitudinal axis of the cartridge. This feeding of the lubricant from outside the cartridge thus takes place within a length portion, as seen along the longitudinal axis, which is at a distance from a front and rear end of the cartridge, as seen in this longitudinal direction. As a result of such a configuration, a more uniform feed of the lubricant into the receiving chamber can take place, and so a better distribution of the lubricant also arises therein. This more uniform distribution and also more uniform introduction of the lubricant is achieved to a particular extent by this first feed duct. Furthermore, with its length defined in this regard, this first feed duct also makes it possible for an auxiliary tool for introducing the lubricant into the first feed duct not to also reach the receiving chamber. This has the additional result that damage to an intraocular lens contained in the cartridge, for example by an injection needle of this auxiliary tool, is prevented, since the injection needle can no longer reach and come into contact with the intraocular lens. Thus, it is also not possible for the intraocular lens to be shifted undesirably in the receiving chamber, as is still possible in previously conventional cartridges. With the cartridge according to the invention, it is therefore possible to avoid a situation in which the intraocular lens is partially pre-folded only by the feed of lubricant.

The invention provides for the first feed duct to be formed in a rib, extending into the receiving chamber, of one cartridge part. As a result, a very exposed component, namely the rib, is provided, which is formed in a similar manner to a pedestal. As a result, it is possible to deliver the lubricant in a targeted manner into an area within the receiving chamber. In this way, the lubricant can be distributed better from a position in the interior of the receiving chamber to the edge of the receiving chamber. This considerably reduces the risk of areas in the receiving chamber not being reached by the lubricant, which could result in the intraocular lens to be delivered being scratched during the subsequent transport in the injector tube.

Provision is advantageously made for the first feed duct to be formed in a rectilinear manner. This has the result that the lubricant can be introduced uniformly into the receiving chamber of the cartridge. There is thus no jerky or pulsed feed of the lubricant. In addition, with a rectilinear feed duct, the probability of the lubricant clogging the feed duct is low.

Provision is preferably made for the rib to extend parallel to the longitudinal axis and, as seen in the direction of the longitudinal axis, to extend at least along half the length of the receiving chamber. In particular, this rib extends along at least 80% of the length of the receiving chamber. The rib extends in particular entirely in a rectilinear manner. As a result of such a geometric configuration of the rib as a rail, the stability of the cartridge part is increased, in particular at a transition between the base element and the wing of a cartridge part.

Provision is made in particular for the rib formed on one cartridge part to have a top side, or inner side, facing the other cartridge part, the first feed duct being formed in an open manner toward the top side and preferably in a channel-like manner in the top side.

In principle, a feed duct should be understood as being a duct that is not closed in the circumferential direction around the longitudinal extent of the feed duct.

In this embodiment, another rib can be used in the other cartridge part in order to reliably cover the channel-like feed duct. Undesired welling out of the lubricant introduced into the first feed duct can be prevented as a result. Furthermore, it is possible, as a result of this configuration, to obtain easy access to this feed duct and to see it or carry out operations therein.

Advantageously, this top side is then configured in a manner transitioning into an inner side of the adjoining wing in a flush manner. As a result mechanical contact with the other cartridge part over a particularly large area can be achieved, such that distribution or undesired welling of the lubricant out of the feed duct outside the receiving chamber is prevented.

Provision is preferably made for the rib to be formed in a wedge-like manner. This specific geometry allows extensive and mechanically stable abutment of the other cartridge part, in particular of a rib applied to the other cartridge part, such that the closed position of the cartridge is also kept particularly stable. Furthermore, this wedge shape also has the result that a flank that faces away from the other cartridge part and thus in particular from the other rib on the other cartridge part is set at an angle. Such a geometry can be used for the mechanical contact with the intraocular lens, such that, when the cartridge is closed, the intraocular lens is pre-folded in the receiving chamber in a predetermined manner.

In particular, provision is made for this rib to be formed at an internal transition between a base element and a wing of one cartridge part. This exposed position of the rib favors the folding operation of the intraocular lens in the cartridge when the latter is closed.

The rib is in particular also a fold stop element which supports the folding operation in the azimuthal direction about the longitudinal axis of the cartridge. This should be understood as meaning that an excessive and thus undesired folded state of the intraocular lens in the receiving chamber is avoided. In the azimuthal direction, this rib thus limits the further folding or rolling up of the intraocular lens. If the cartridge parts are moved together such that the cartridge is closed, pre-folding of the intraocular lens in the receiving chamber takes place, wherein the rib on one cartridge part, preferably a rib on each cartridge part, forms an azimuthal fold stop element.

When viewed in a plane perpendicular to the longitudinal axis of a cartridge, a rib thus has a triangular shape as preferred geometry.

In particular, provision is made for the first feed duct to be covered, in the closed state of the cartridge, by a planar top side or inner side of a further rib formed on the other cartridge part. This is advantageous, since the first feed duct is thus necessarily also closed with the cartridge closed and then, when lubricant is fed via the feed duct after the closed state has been achieved, it is not possible for the lubricant to escape radially. In the closed state of the cartridge, the feed duct is thus closed in the radial direction. If the feed duct is formed in a channel-like manner, the duct is freely accessible in the radial direction with respect to the longitudinal axis of the feed duct on account of the channel shape in the open state of the cartridge.

Preferably, provision is made for a further rib that extends into the receiving space or the receiving chamber to be formed in the other cartridge part, a second feed duct being formed in the further rib. In the closed state of the cartridge, the feed ducts are arranged in a congruent manner and thus cover one another. The volume of an overall feed duct formed from the two feed ducts is then enlarged compared with a single feed duct. As a result, a larger amount of lubricant can be introduced more quickly into the receiving chamber. Nevertheless, in the open state of the cartridge, each of the feed ducts is freely accessible when the latter is formed in a channel-like manner.

In an advantageous embodiment, provision is made for the first feed duct to be formed in one cartridge part and a continuous filling hole to be formed in the cartridge part or in the further cartridge part. The filling hole is formed in a manner leading into the first feed duct in the closed state of the cartridge, and in the closed state of the cartridge, this filling hole leads toward the outside and is thus accessible from the outside. This filling hole thus allows lubricant to be introduced into the cartridge. Moreover, with the cartridge closed, the first feed duct is not directly accessible from the outside and does not lead directly toward the outside. It is only as a result of the coupling and thus the cooperation between the filling hole and the first feed duct that an overall path is created, through which the lubricant is able to be passed into the receiving chamber from outside the cartridge. As a result of this particularly advantageous embodiment, it is possible for a subcomponent of the lubricant feed device to be created in each of the different cartridge parts, wherein the advantages already mentioned above are generated in each case all by themselves. As a result of this configuration, the feed of the lubricant into the receiving chamber is achieved to a particular extent without undesired contact and without undesired shifting of the intraocular lens by an auxiliary tool for introducing the lubricant.

Provision can be made, in a closed state of the cartridge, for a hole axis of the filling hole and a longitudinal axis of the first feed duct not to be parallel to one another and not to be coaxial with one another. This is a further, very advantageous embodiment, since, as a result of this arrangement at an angle other than 0° and other than 180°, at least one bend is formed on the overall path on which the lubricant is introduced into the receiving chamber from outside the cartridge. This configuration then has the result that, for example, an injection needle of an auxiliary tool could never reach the receiving chamber and come into contact with the intraocular lens therein. At most, this injection needle can then reach a penetration depth which corresponds to the depth of the filling hole, with the result that, on account of the other course or the other orientation of the at least first feed duct, this injection needle is then prevented from moving any further.

Advantageously, provision is made for the hole axis of the filling hole to be arranged in an inclined manner at an angle of between 90° and 160°, in particular between 100° and 130°, to a longitudinal axis of the first feed duct.

Advantageously, provision is made for a hole axis of the filling hole to be arranged in an inclined manner at an angle of between 90° and 160° to a longitudinal axis of the feed duct of that cartridge part in which the filling hole is formed. This allows easy positioning of an auxiliary tool, in particular of an injection needle of an auxiliary tool, with respect to the cartridge and also favors the passage of the lubricant from the filling hole into a feed duct and from there into the receiving chamber.

Provision can be made for at least the first feed duct to be oriented at an angle of between 60° and 120°, in particular between 80° and 100°, to the longitudinal axis of the cartridge. As a result, a relatively short first feed duct is formed. Clogging of the feed duct with the lubricant is avoided as a result.

Preferably, the first feed duct is formed in a non-rectilinear manner along its duct axis and is formed in a manner curved at least once or in a manner extending at an angular offset. Such a configuration increases the flow resistance of the feed duct and, in the case of a lubricant of low viscosity, can limit the speed at which the lubricant passes into the receiving chamber.

Advantageously, provision is made for the at least first feed duct to lead, with an end facing away from the receiving chamber, toward the outside at the wing of one cartridge part in the closed state of the cartridge, and for the first feed duct to be formed in particular entirely in a rectilinear manner. With such an embodiment, an inlet of the at least first feed duct is then formed between the two wings, resting against one another, of the cartridge parts. Advantageously, provision is then made here for those ends of the wings that are remote from the base elements to be curved slightly away from one another and thus not to be in direct contact. This results in a beak-like or Y-shaped spreading apart at these ends of the cartridge parts that are remote from the base elements, with the result that an auxiliary tool can be passed easily to this inlet of this feed duct.

Provision may also be made for at least the first feed duct to extend partially parallel to the longitudinal axis of the cartridge. As a result, the lubricant can be fed optimally into the receiving chamber in a manner depending on the geometry of the intraocular lens.

In an advantageous embodiment, provision is made for an end, close to the receiving chamber, of the at least first feed duct to be formed in a narrowed manner. As a result, any penetration of the auxiliary tool, in particular of an injection needle of an auxiliary tool, into the receiving chamber can be avoided in an even better manner. This narrowing is thus formed in particular in such a way that an inside diameter is less than an outside diameter of such an injection needle of an auxiliary tool.

This embodiment is particularly advantageous when the at least first feed duct is formed entirely in a rectilinear manner.

Preferably, the cartridge is formed in one piece with the cartridge parts, in particular from plastic. The cartridge parts are preferably connected directly together. To this end, provision can be made for at least one film hinge to be formed for this purpose. This film hinge is formed in particular at the ends of the base elements which are remote from the respective wings of the cartridge parts.

In a further advantageous embodiment, provision can be made for the radial extent, and thus an extent perpendicular to a longitudinal axis of the cartridge, of a rib on one cartridge part to be different than this radial extent of the rib on the other cartridge part. In this way, a radial offset or overhang is formed at the ends facing the receiving chamber or front edges of these ribs, with the result that an alternative configuration with regard to the fold stop element is achieved. It is also possible for a feed duct then to be formed in that top side of a rib that extends radially further into the receiving chamber, such that this feed duct then also leads into the receiving chamber partially in a radially exposed manner, since it also extends in the offset or overhang and in particular then leads into the receiving chamber via the offset. This allows more comprehensive introduction of lubricant.

Preferably, the first feed duct extends along an entire length of a rib, extending into the receiving chamber, of a cartridge part. In this way, a uniform input, over a relatively long section, of lubricant into the receiving space of the cartridge can be achieved.

Furthermore, the invention also relates to an injector for introducing an intraocular lens into an eye, the injector having a cartridge according to the abovementioned invention or an advantageous configuration thereof. The cartridge can be provided as a separate part which is then configured to be inserted in a loading area of the injector, in particular in a loading area of an injector tube.

Advantageously, provision is made for the cartridge to be formed integrally and thus in one piece with an injector tip of the injector for implanting an intraocular lens in an eye. The injector tip in this case represents that component of the injector that is introduced into the eye with its front end, in order then to introduce the intraocular lens by means of the injector via the injector tip. In particular, provision is made for one of the cartridge parts to be connected to the injector tip in a positionally fixed manner and thus for no relative movement between the injector tip and this cartridge part to be allowed. The further cartridge part(s) that then remain(s) is/are then pivotable relative to the injector tip and to the other cartridge part.

In particular, provision is made for the cartridge part that is pivotable relative to the other cartridge part and to the injector tip to be formed with the filling hole.

The injector preferably also has a plunger which is axially displaceable. By means of this plunger, the intraocular lens can then be pushed axially out of the cartridge in the direction of an injector tip of the injector. In particular, the intraocular lens that has already been pre-folded in the cartridge by the closing operation of the cartridge is then brought into its final folded position on the further pushing-out path in the injector tip, and can then be introduced into the eye in a correspondingly folded manner on emerging from the injector tip.

The indications "top", "bottom", "front", "rear", "horizontal", "vertical", "outer", "inner", et cetera, indicate given positions and orientations when the cartridge is used as intended and arranged as intended, in particular on an injector for injecting an intraocular lens into an eye.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
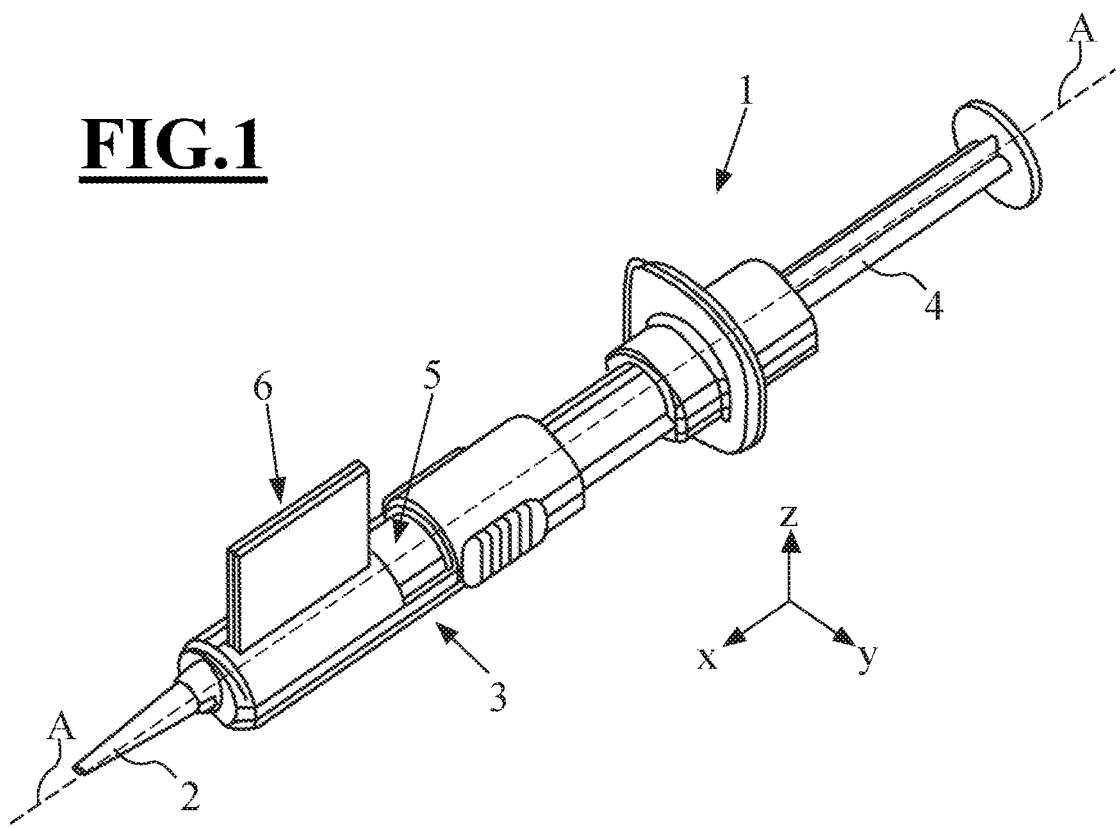
FIG. 1 is a perspective view of an embodiment of an injector according to the invention with an embodiment of a cartridge according to the invention.

In the FIGS., identical or functionally identical elements are provided with the same reference characters.

FIG. 1 shows a perspective view of an injector 1. The injector 1 is configured to introduce an intraocular lens into an eye. The illustration, to be understood to be merely schematic, of the injector 1 shows an injector tip 2, which is arranged at the front in the direction of a longitudinal axis A of the injector 1. The injector tip 2 is then introduced into part of the eye during an implantation and the intraocular lens is implanted into the eye via the injector tip 2.

The injector 1 furthermore includes an injector tube 3, which rearwardly adjoins the injector tip 2 in the axial direction. The injector 1 furthermore includes a plunger 4, which is displaceable in the injector tube 3 in the direction of the longitudinal axis A. Also formed in the injector tube 3 is a loading area 5 in which a cartridge 6 is insertable or is fixedly positioned therein.

The intraocular lens to be implanted is received in the cartridge 6. The cartridge 6 is open at the front and rear in the axial direction and thus in the direction of the longitudinal axis A, such that the intraocular lens located therein can be pushed out of the cartridge 6 by the plunger 4 in the direction of the injector tip 2 and can be pushed into the injector tip 2.

The cartridge 6 as such can be a separate component. It can also be formed in one piece with the injector tip 2, however.

Figure 2:
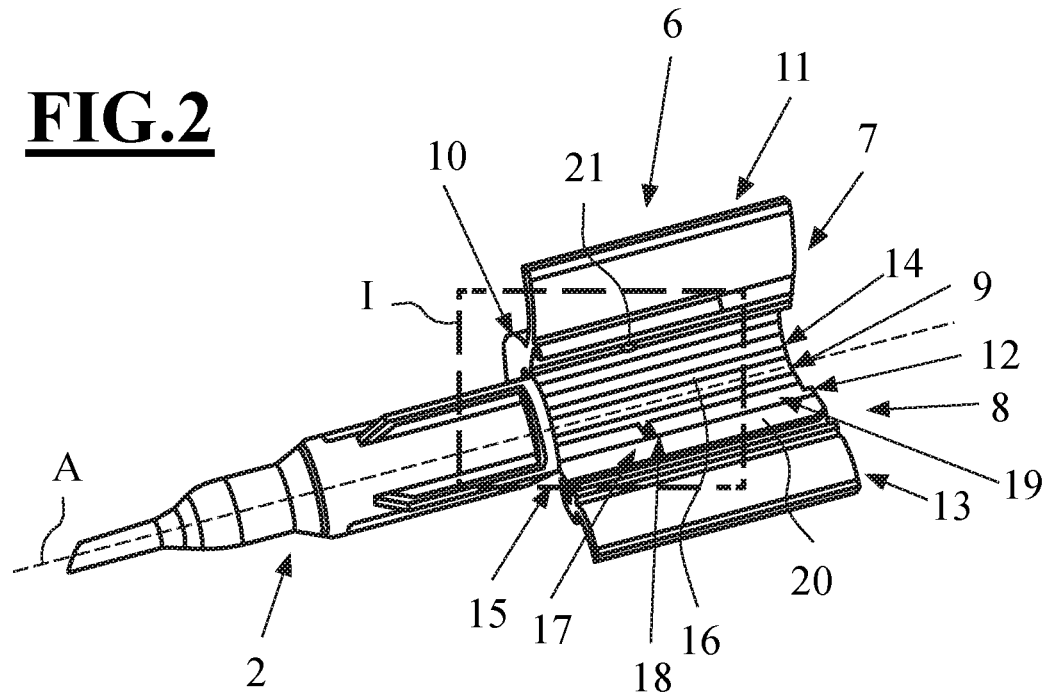
FIG. 2 is a perspective view of a first embodiment of a cartridge according to the invention in the open state.

FIG. 2 is a perspective view of a first embodiment of the cartridge 6.

In general, the cartridge 6 is formed as an integral component, in particular made of plastic, in all embodiments.

In the example shown in FIG. 2, the cartridge 6 is formed in one piece with the injector tip 2. However, it can also be formed separately therefrom. These two possibilities are also possible for the embodiments explained below.

The cartridge 6 includes a cartridge part 7 and a further cartridge part 8. The two cartridge parts 7 and 8 are pivotable relative to one another about a longitudinal axis of the cartridge 6, which corresponds to the longitudinal axis A. In this embodiment, the cartridge parts 7 and 8 are connected directly together, in particular via a film hinge 9. However, the cartridge parts 7 and 8 can also be connected to one or more holder elements, wherein the cartridge parts 7 and 8 are pivotable about this holder element or these holder elements.

The cartridge part 7 includes a channel-like or bulbous base element 10 and a wing 11 adjoining the latter. The wing 11 is formed in a plate-like manner.

The cartridge part 8 likewise includes a channel-like or bulbous base element 12 and a wing 13 adjoining the latter. The cartridge 6 is formed in an open manner both at an axial rear end 14 and at an axial front end 15. The axial front end 15 leads out directly at the injector tip 2.

In FIG. 2, the cartridge 6 is shown in the open state. If the cartridge 6 is closed, the two cartridge parts 7 and 8 are pivoted toward one another about the axis A and the two wings 11 and 13 are connected together, in particular by means of a snap connection.

On account of the channel-like base elements 10 and 12 that are curved in opposite directions, a tubular receiving chamber 16 for the intraocular lens is formed in the closed state of the cartridge 6.

In order to push the intraocular lens out of the cartridge 6 into the injector tip 2 with as little friction as possible out of the injector, a lubricant, in particular a viscoelastic medium, in particular an OVD, is introduced into the cartridge.

This takes place in the closed state of the cartridge 6. Since, as regards accessibility, it is difficult to feed this lubricant particularly in the closed state of the cartridge 6, a lubricant feed device 17 is provided, which allows this in a correspondingly simple manner. Furthermore, in the closed state of the cartridge, as a result of the lubricant feed device 17, the lubricant fed into the receiving chamber 16 is also introduced and distributed as uniformly as possible, such that the intraocular lens located therein is not shifted in an undesired manner or a further folding operation of the lens is not impaired in an undesired manner.

Figure 3:
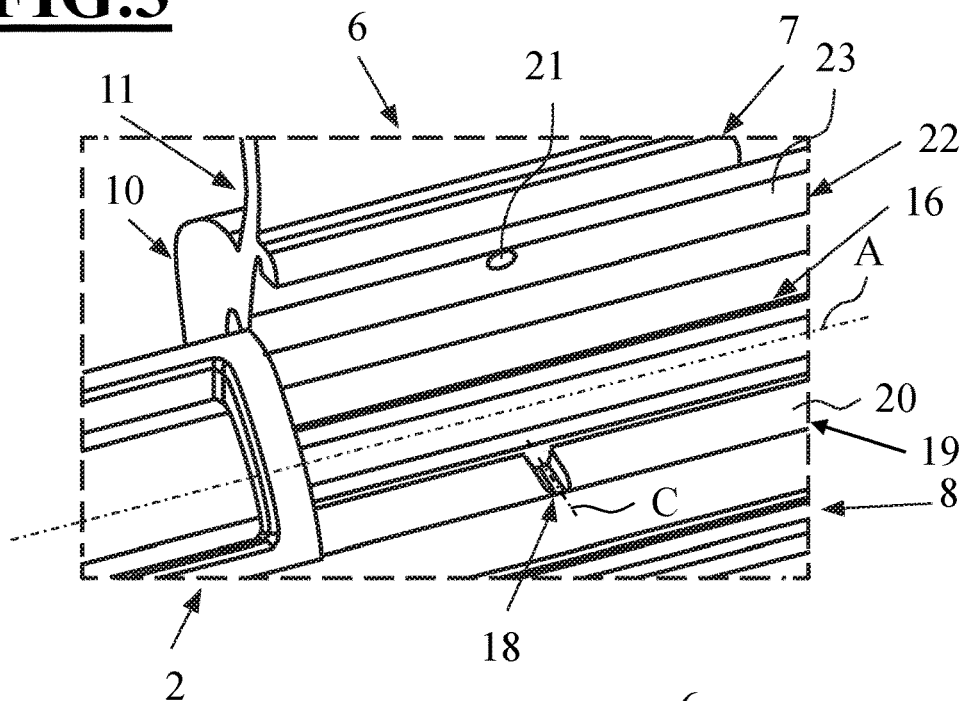
FIG. 3 shows an enlarged illustration of the view in FIG. 2.

To this end, the lubricant feed device 17 has, in the embodiment shown in FIG. 2, a first feed duct 18, which is formed in a channel-like manner in this embodiment, cf. also FIG. 3. This first channel-like feed duct 18 is formed in the cartridge part 8. In the embodiment shown, the cartridge part 8 is the one which is connected to the injector tip 2 in a positionally fixed manner. By contrast, the cartridge part 7 is pivotable relative to the injector tip 2 and to the cartridge part 8.

The first channel-like feed duct 18, which, on account of the channel shape, is a radially not completely closed duct, extends along a longitudinal axis C. This longitudinal axis C is, in the embodiment shown in FIG. 3, oriented at an angle of between 80° and 100°, in particular 90°, to the longitudinal axis A. This first channel-like feed duct 18 thus leads radially into the receiving chamber 16 and is configured in a rectilinear manner.

Formed on the cartridge part 8 is a rib 19, which extends radially into the receiving chamber 16. This rib 19 is, in the embodiment, formed parallel to the longitudinal axis A and formed in particular along the entire axial length of the cartridge part 8. The rib 19 has a top side 20, which is formed in particular in a planar manner. This top side 20 thus also forms an inner side, which faces the cartridge part 7 in the closed state of the cartridge 6. The first channel-like feed duct 18 is formed in this top side 20 and formed so as to open upwardly and out of the top side 20. It is thus formed in an open manner facing the cartridge part 7 along its entire extent and thus its entire length.

In the embodiment illustrated in FIG. 3, the first channel-like feed duct 18 is formed entirely in a rectilinear manner. In the closed state of the cartridge 6, this first channel-like feed duct does not lead toward the outside, and so it is not directly accessible from the outside.

Provision can also be made for the channel-like feed duct 18 to be formed in a non-rectilinear manner along its duct axis. The channel-like feed duct 18 can, according to a further embodiment, be curved once or several times and thus be formed in a "serpentine" manner, or be provided with an angular offset along its duct axis. Such a configuration increases the flow resistance of the feed duct and, in the case of a lubricant of low viscosity, can limit the speed at which the lubricant passes into the receiving chamber.

The lubricant feed device 17 furthermore comprises a filling hole 21, which is formed in the cartridge part 7, such that the filling hole 21 and the first channel-like feed duct 18 are formed in different cartridge parts.

The filling hole 21 is configured as a continuous hole and leads toward the outside in the closed state of the cartridge 6. The filling hole 21 is configured such that, in the closed state of the cartridge 6, the filling hole 21 leads radially into the first channel-like feed duct 18, or corresponds thereto such that a lubricant fed via the filling opening, or the filling hole 21, passes into the first channel-like feed duct 18 and is introduced from there into the receiving chamber 16.

FIG. 3 shows an enlarged illustration of a detail I in FIG. 2. The filling hole 21 is in this case formed in a rib 22 on the cartridge part 7. The rib 22 is likewise formed in a wedge-like manner and extends along the entire extent of the cartridge part 7 in the direction of the longitudinal axis A. The rib 22 has a top side 23, or an inner side, which bears against the top side 20 of the rib 19 in the closed state of the cartridge 6. The rib 22 is formed at an internal transition between the base element 10 and the wing 11. In a corresponding manner, the rib 19 is also formed at an internal transition between the base element 12 and the wing 13. The ribs 19 and 22 also form fold stop elements, such that the pre-folding of the intraocular lens in the cartridge 6 itself is limited in the azimuthal direction when the cartridge 6 is closed.

Given that the top sides 20 and 23 rest extensively against one another in the closed state of the cartridge 6, the first channel-like feed duct 18 is also closed in a radial direction along its length, in particular completely closed along this length.

Figure 4:
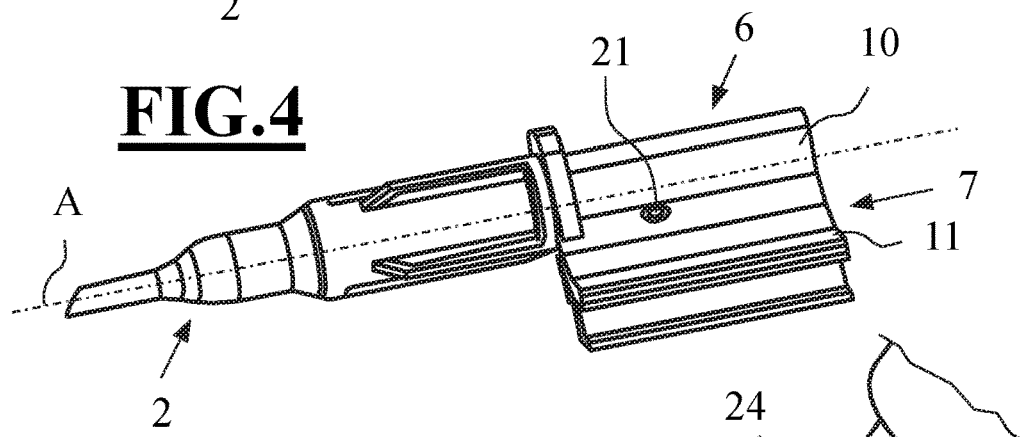
FIG. 4 is a perspective view of the cartridge according to FIG. 2 and FIG. 3 in the closed state.

FIG. 4 shows the configuration of the module with the injector tip 2 and the cartridge 6 in the closed state of the cartridge 6. A mouth opening of the filling hole 21 can be seen. Therefore, a very specific interface and junction point for introducing the lubricant is locally created on the cartridge 6.

As a result, in this embodiment and in all further embodiments, the mouth opening of the filling hole 21 is particularly advantageously provided outside the base element.

The first channel-like feed duct 18 is arranged on an opposite side from the film hinge 9. Therefore, lubricant is not introduced in the region of the film hinge 9 or in the region of ends of the base element 10 that are remote from the wings 11 and 13. As a result of this configuration, the lubricant is also always introduced into the receiving chamber 16 from the side which does not impede the desired folding direction of the intraocular lens toward the base elements 10 and 12, but favors this. Therefore, the pre-folded state, achieved upon closing of the cartridge 6, of the intraocular lens is not partially undone or brought about in the opposite direction by the introduction of the lubricant. Rather, as a result of the then deliberate and cross-sectionally U-shaped pre-folding of the intraocular lens, the lubricant can be introduced into the area that is open on account of the U shape of the pre-folded intraocular lens, such that the pre-folded state of the intraocular lens is even supported by the lubricant. The distribution of the lubricant is then also accordingly favored in this regard, such that uniform distribution and uniform introduction into the receiving chamber 16 is achieved, and thus an improved pushing-out behavior of the intraocular lens out of the receiving chamber 16 is then brought about.

Figure 5:
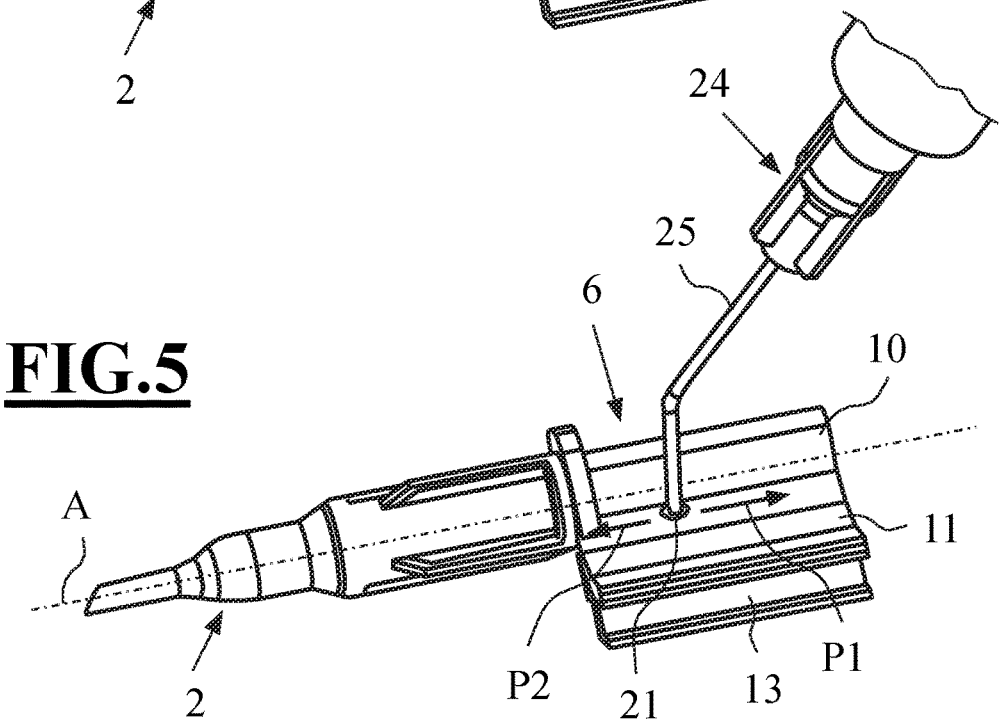
FIG. 5 shows a schematic according to FIG. 4 with an additional auxiliary tool for introducing a lubricant into the cartridge.

FIG. 5 shows a perspective illustration of an auxiliary tool 24 which is formed with an injection needle 25. By means of this auxiliary tool 24, the lubricant located therein is introduced into the cartridge 6, external thereto, via the filling opening 21 and the first channel-like feed duct 18 into the receiving chamber 16. The in this regard uniform distribution of the lubricant is indicated by the arrows P1 and P2 that are indicated only by way of example.

Figure 6:
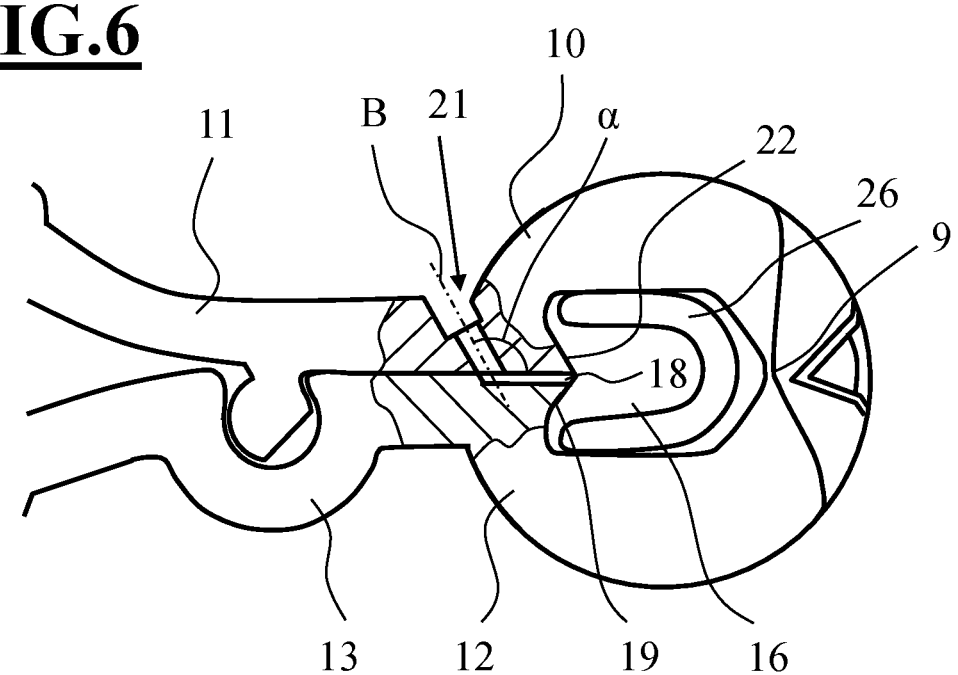
FIG. 6 is a cross-sectional view perpendicularly to the longitudinal axis of the cartridge according to FIG. 2 to FIG. 5 in the closed state of the cartridge and with a pre-folded intraocular lens contained in a receiving chamber of the cartridge.

FIG. 6 shows a schematic sectional illustration, in a section plane perpendicular to the longitudinal axis A, of the cartridge 6 according to the first embodiment in the closed state. As can be seen, a hole axis B is oriented at an angle a to a longitudinal axis C of the first channel-like feed duct 18. The angle a is preferably between 90° and 140°.

Furthermore, the extent of the ribs 19 and 22 in the direction of the receiving chamber 16 can also be seen in FIG. 6, the ribs 19 and 22 having stop faces, inclined with respect to the horizontal, for the intraocular lens. These stop faces form a stop element which serves as an azimuthal stop for the intraocular lens 26, which is shown in FIG. 6 in a state pre-folded in a U shape in the closed receiving chamber 16. It can also be seen that, as a result of this pre-folded state, the intraocular lens 26 is bent toward the film hinge 9 and the opening of the U shape arises toward the rib 19 and toward the rib 22. As a result of this position and the configuration of the lubricant feed device 17, it is then possible for the lubricant to be introduced in a targeted manner into this clearance of the folded intraocular lens 26 and be distributed comprehensively in the receiving chamber 16.

In this first embodiment, the channel-like feed duct 18 is provided only in the rib 19. Only the filling opening 21 is provided in the rib 22. In the closed state of the cartridge 6, it is thus possible to deliver the lubricant from the filling opening 21 to the channel-like feed duct 18 and from there into the receiving chamber 16.

Figure 7:
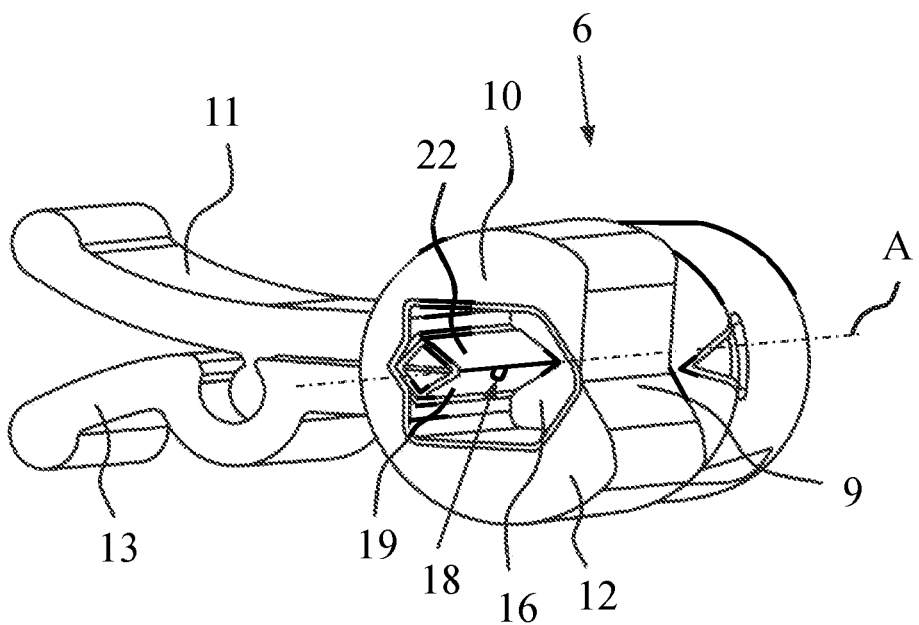
FIG. 7 is a perspective view of the first embodiment of the cartridge according to FIGS. 2 to 6.

FIG. 7 shows a perspective illustration of the cartridge 6 according to the first embodiment. In particular, the ribs 19 and 22 with their inclined stop faces are readily discernible. The junction of the first channel-like feed duct 18 into the receiving chamber 16 is also shown.

Figure 8:
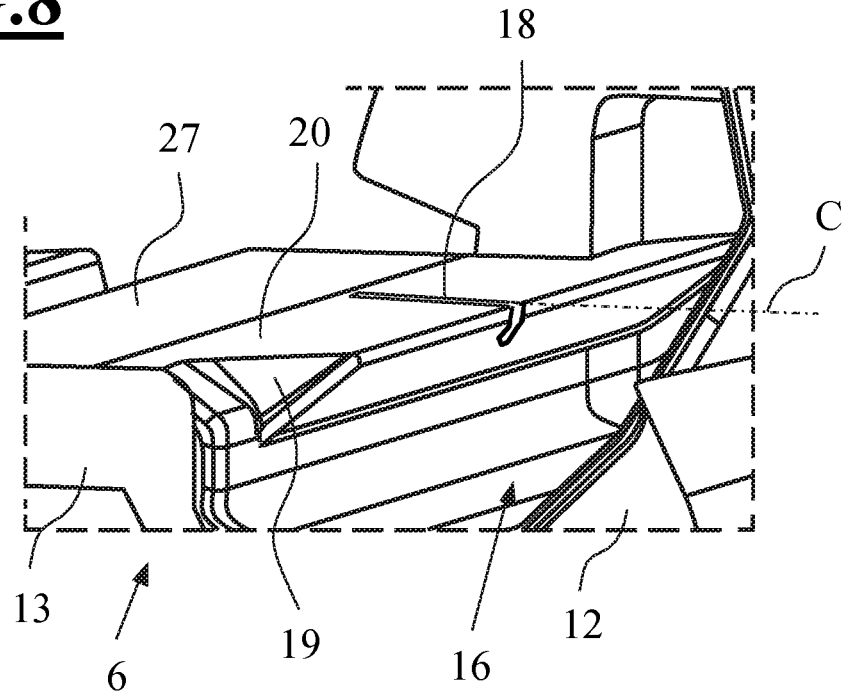
FIG. 8 shows an enlarged schematic of a detail of the cartridge according to FIG. 2 to FIG. 7.

FIG. 8 shows an enlarged illustration of a detail of the cartridge 6 in the region of the rib 19 with the first channel-like feed duct 18, wherein the cartridge 6 is in the open state. It can be seen that the top side 20 transitions in a flush manner into a top side, or inner side, 27 of the wing 13. As can furthermore also be seen, the first channel-like feed duct 18 extends with its longitudinal axis C perpendicular to the longitudinal extent of the rib 19. However, the feed duct 18 can also extend beneath the top side 20 and is then no longer channel-like, but formed in a closed manner around its entire circumference. The feed duct then forms a blind hole, which corresponds to the filling hole 21 in the closed state of the cartridge 6.

Figure 9:
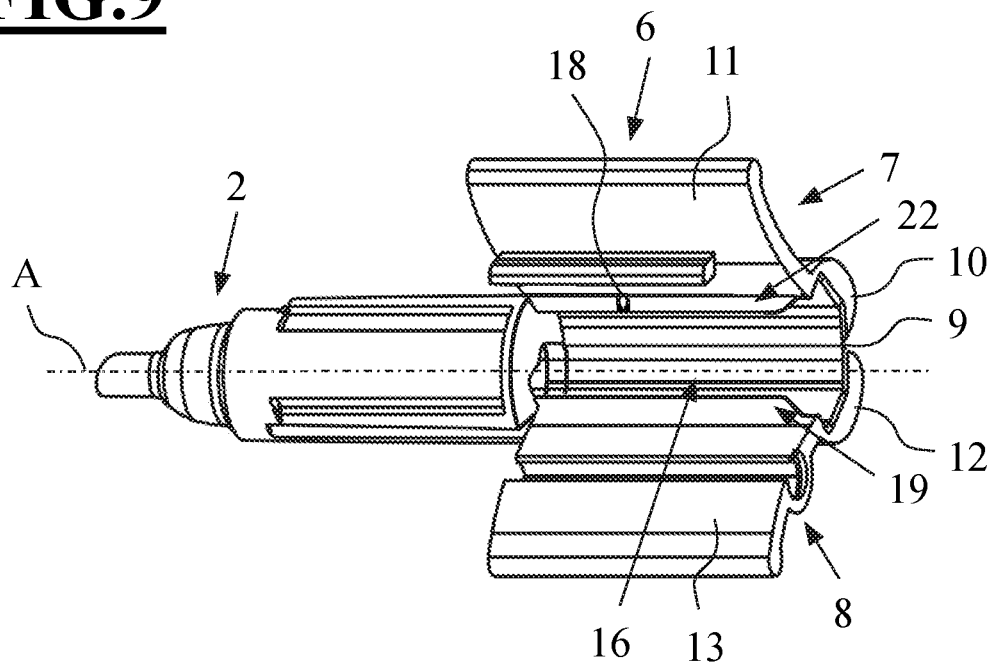
FIG. 9 shows a perspective view of a second embodiment of a cartridge according to the invention.
Figure 10:
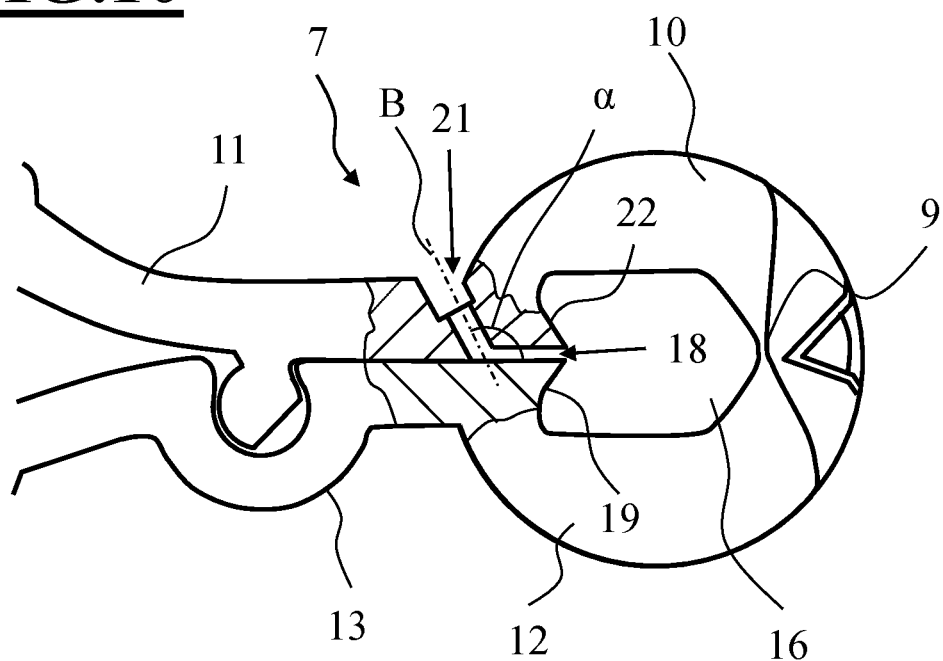
FIG. 10 shows a cross-sectional view of the cartridge according to the second embodiment in the closed state of the cartridge.

FIG. 9 shows a perspective view and FIG. 10 shows a cross section of a second embodiment of a cartridge 6 in the open state. Here too, an integral configuration of the cartridge 6 with the injector tip 2 is shown by way of example, although this can also be configured in some other way and the cartridge 6 can be in the form of a separate part. In contrast to the first embodiment, provision is made here for both the first channel-like feed duct 18 and the filling hole 21 to be formed in a common cartridge part, in particular in the cartridge part 7. The hole axis B of the filling hole 21 is formed at an angle a of preferably 90° to 140° to the longitudinal axis C of the channel-like feed duct 18. The cartridge part 7 is the pivotable cartridge part.

Figure 11:
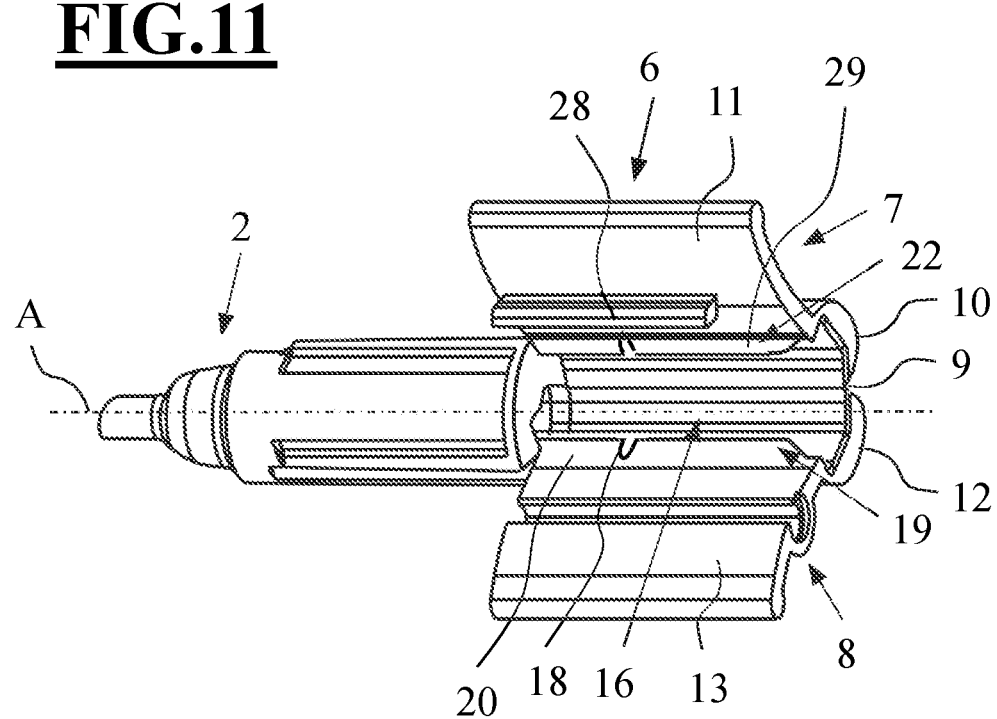
FIG. 11 shows a perspective view of a third embodiment of a cartridge according to the invention in the open state of the cartridge.

FIG. 11 shows a perspective illustration of a third embodiment of a cartridge 6 in the open state. By way of example, the cartridge 6 is again connected in one piece to the injector tip 2 here. In this configuration, provision is made for a first channel-like feed duct 18 to be formed in the cartridge part 8 and thus in the fixed cartridge part 8. In particular, it is formed in the rib 19, as has already been explained in the previous embodiments.

Furthermore, the filling hole 21 is formed in the cartridge part 7. In addition, provision is made here for a second channel-like feed duct 28 also to be formed in this cartridge part 7. The lubricant feed device 17 thus comprises the channel-like feed duct 18 and the channel-like feed duct 28. The filling hole 21 leads directly into the second channel-like feed duct 28. This second channel-like feed duct 28 is formed in particular in the rib 22 and formed in an open manner toward the top side 23. In the closed state of the cartridge 6, provision is made here for the top sides 23 and 20, as in the first embodiment, to rest extensively on one another and for the channel-like feed ducts 18 and 28 to be formed such that, in the closed state of the cartridge 6, they rest congruently on one another. Therefore, they cover one another. As a result, a cross-sectionally and thus volumetrically larger overall feed duct is formed from the two channel-like feed ducts 18 and 28. The second channel-like feed duct 28 also extends along a length which corresponds to the width of the rib 22 and is thus in the form of a blind duct which leads into the receiving chamber 16 only with one open end, as seen in the axial direction of the second channel-like feed duct 28.

Figure 12:
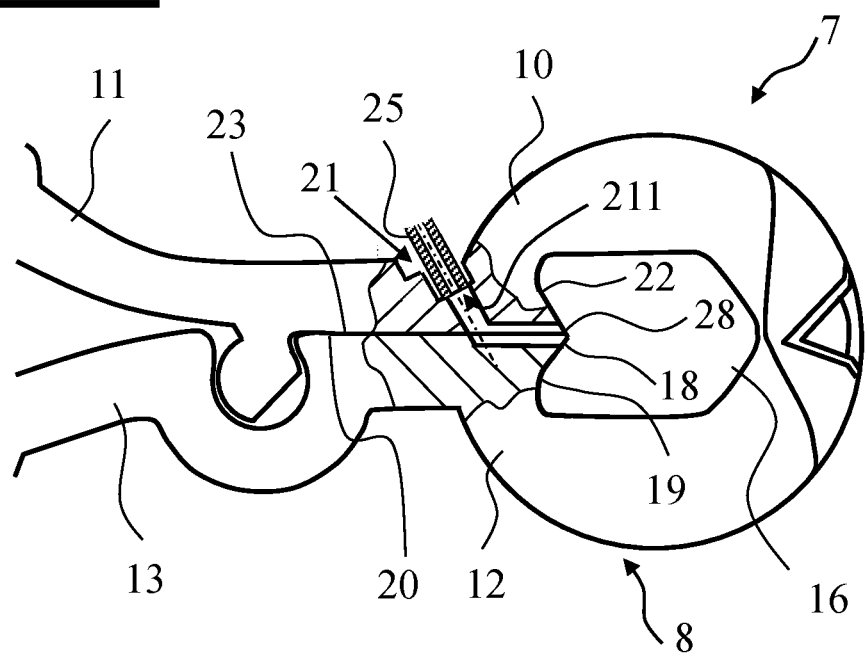
FIG. 12 shows a cross-sectional view of the third embodiment of the cartridge according to the invention in the closed state.

FIG. 12 shows the third embodiment of the cartridge 6 in the closed state in cross section, wherein an intraocular lens is not illustrated in the receiving space 16. Furthermore, the injection needle 25 of the auxiliary tool 24 is shown in FIG. 12. It can be seen here that complete penetration into the receiving chamber 16 can never occur even at a corresponding penetration depth of the injection needle 25 into the filling hole 21. The injection needle 25 can be advanced at most as far as a bottom 211 of the filling hole 21. This is advantageous since, in this way, it is not possible for there to be any contact entailing possible damage to an intraocular lens 26 in the receiving space 16.

Figure 13:
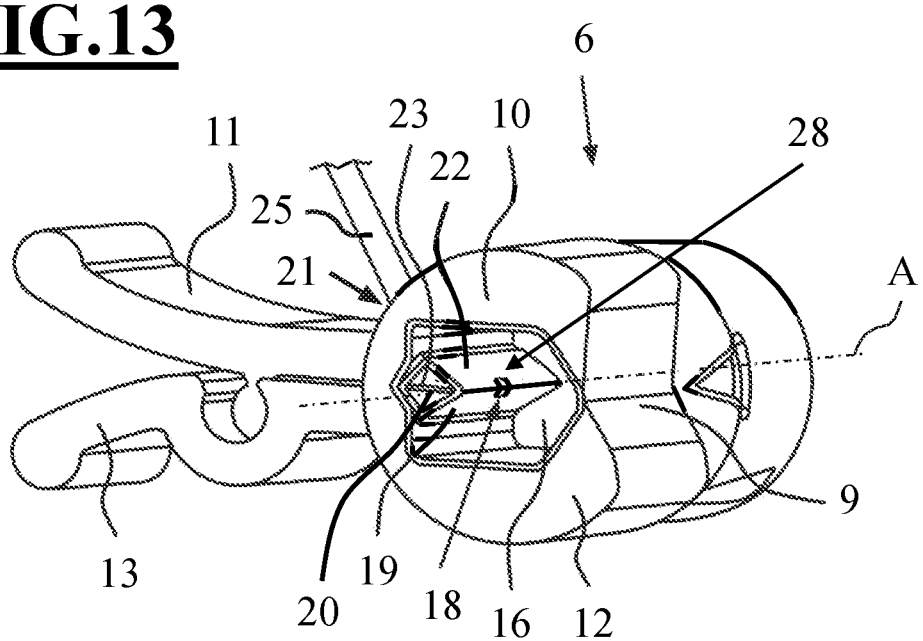
FIG. 13 shows a perspective view of the cartridge according to FIG. 12 in the closed state.

FIG. 13 shows a perspective illustration of the third embodiment including the injection needle 25, wherein, in this case, the cartridge 6 is illustrated in the closed state. The direct resting of the top sides 20 and 23 on one another is shown here.

Figure 14:
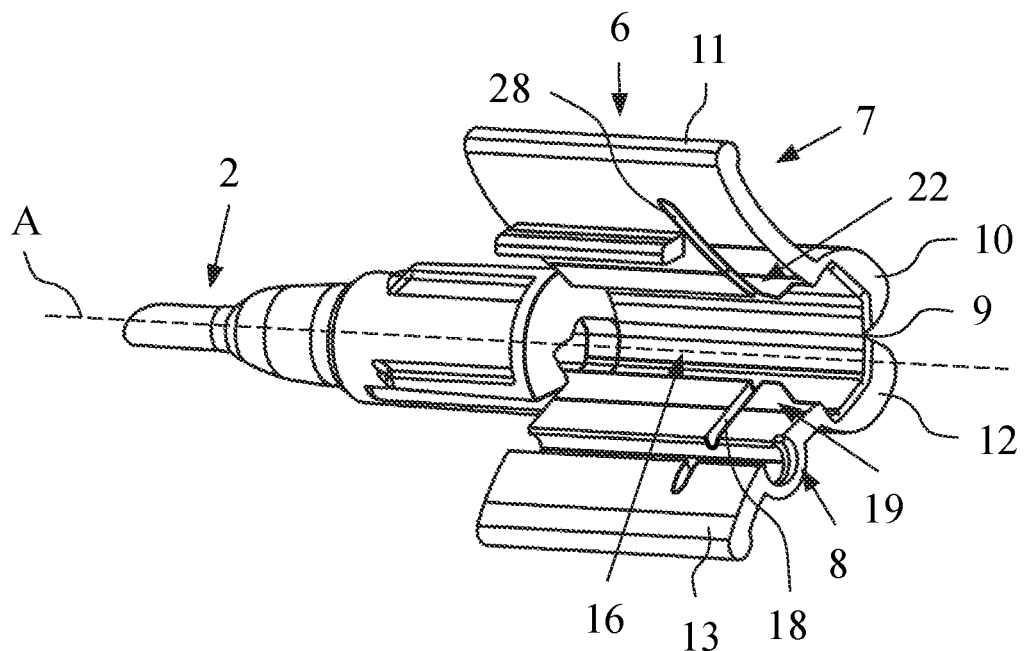
FIG. 14 shows a perspective view of a fourth embodiment of a cartridge according to the invention in the open state.

FIG. 14 shows a perspective illustration of a fourth embodiment of a cartridge 6. Here too, an integral configuration with the injector tip 2 is provided by way of example.

In this configuration, the lubricant feed device 17 is formed with a first channel-like feed duct 18, which is formed in the cartridge part 8. A second channel-like feed duct 28 is formed in the cartridge part 7. The two channel-like feed ducts 18 and 28 are formed entirely in a rectilinear manner.

The first channel-like feed duct 18 extends along a longitudinal axis C which is oriented at an angle of between 80° and 100°, in particular 90°, to the longitudinal axis A. The first channel-like feed duct 18 extends from the receiving chamber 16 in a direction of a free outer end of the wing 13. The length of the first channel-like feed duct 18 is chosen such that, in the closed state of the cartridge 6, this channel-like feed duct 18 is accessible directly from the outside. The same also goes for the second channel-like feed duct 28.

Figure 15:
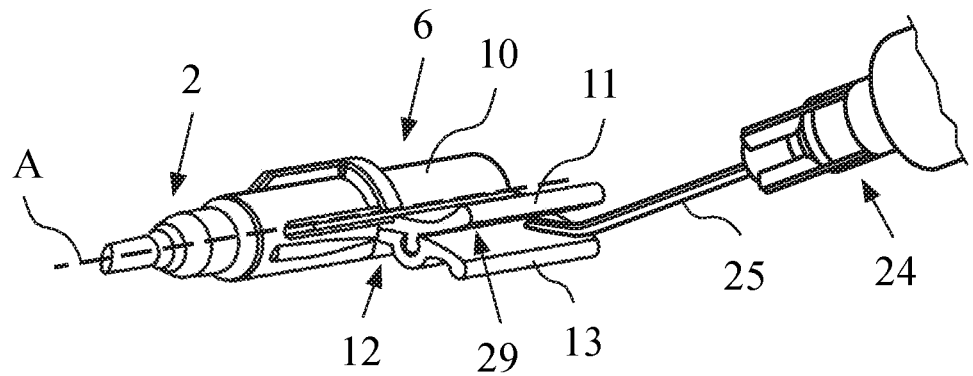
FIG. 15 shows a perspective view of the cartridge according to FIG. 14 in the closed state and with an additional auxiliary tool for introducing a lubricant into the cartridge.
Figure 16:
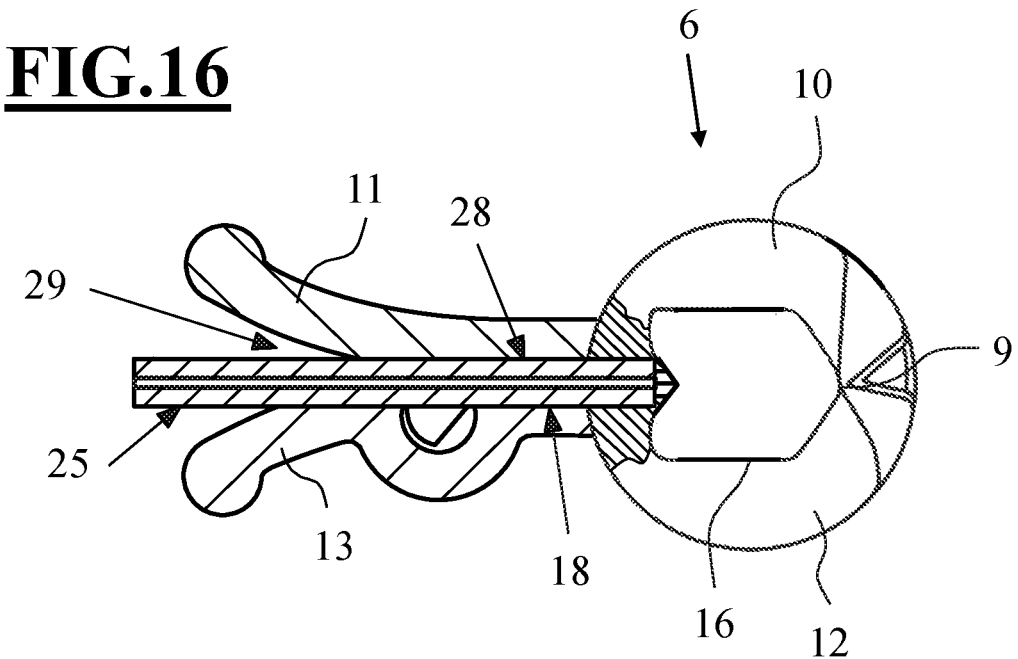
FIG. 16 shows a cross-sectional view perpendicularly to the longitudinal axis of the cartridge according to FIG. 15.

In this embodiment, as is illustrated in FIG. 15 and FIG. 16, in the closed state of the cartridge 6, the injection needle 25 can thus be introduced at an inlet point 29 directly into the overall feed duct which is formed from the two channel-like feed ducts 18 and 28.

As can furthermore be seen in FIGS. 14 and 15, the wings 11, 13 are curved away from one another at their free ends remote from the base elements 10 and 12, such that a beak-like widening arises, into which the injection tip 25 can be introduced. As a result of this configuration, the overall feed duct ends before the free ends of the wings 11 and 13. As a result, it is also protected to a certain extent and the introduction of the injection needle 25 is accordingly possible in an expedient manner and as a result also guided in a corresponding manner.

FIG. 16 shows a schematic cross-sectional illustration perpendicular to the longitudinal axis A of the configuration of the cartridge 6 according to FIGS. 14 and 15.

Figure 17:
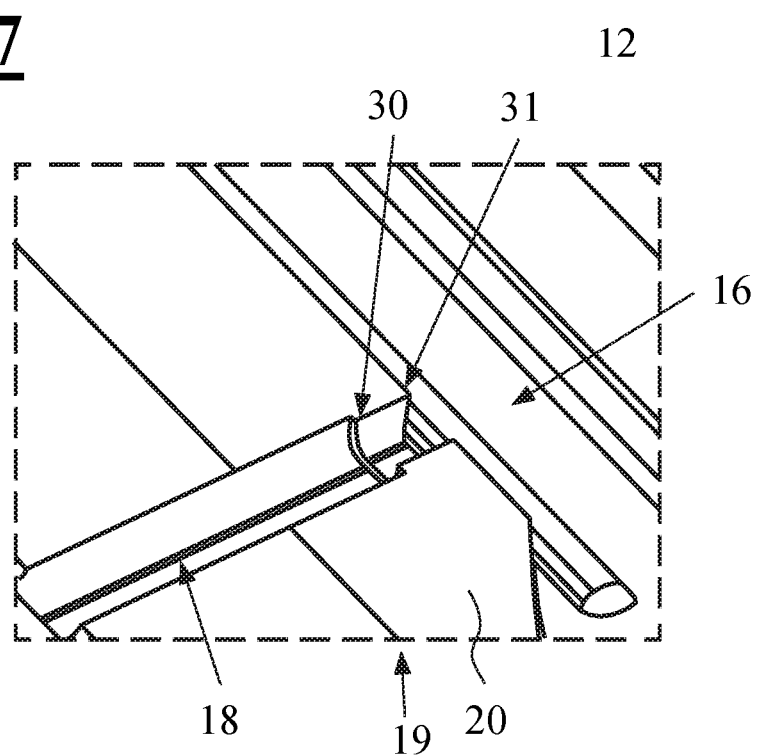
FIG. 17 shows an enlarged illustration of a part of the cartridge according to FIG. 14 to FIG. 16 with an enlarged illustration of a feed duct.

In order, in particular in this embodiment, although it can also be possible in other embodiments, to avoid any passage of the injection needle 25 into the receiving chamber 16, at least one channel-like feed duct 18 and/or 28 is formed, at its end 30 that leads into the receiving chamber 16, with a narrowing 31; see FIG. 17. In particular, both channel-like feed ducts 18 and 28 can be formed in a narrowed manner at their ends that face the receiving chamber 16 and lead into the receiving chamber 16. The narrowing is in this case of such a kind that a reduction in diameter is achieved, such that the injection needle 25 is stopped at the narrowing 31 upon introduction into the overall feed duct and cannot pass into the receiving chamber 16. The narrowing 31 can be configured as a discrete step or as a continuous, for example conical narrowing.

Furthermore, in a further embodiment, provision can also be made for the ribs 19 and 22 to be formed with different dimensions in the radial direction and thus toward the longitudinal axis A, and thus for an edge facing the receiving chamber 16 or a free end of a rib 19 or 22 to extend further into the receiving chamber 16 than is the case for the other rib. With such a radial overhang into the receiving chamber 16, the functionality as a fold stop can be individualized further. In particular, provision is then made for the first channel-like feed duct 18 to be formed in the rib which extends further into the receiving chamber 16 than the other rib. As a result, not only is an axial opening of this channel-like feed duct obtained, but furthermore also a radial opening is obtained, this being achieved by the overhang of this rib compared with the other rib.

Figure 18:
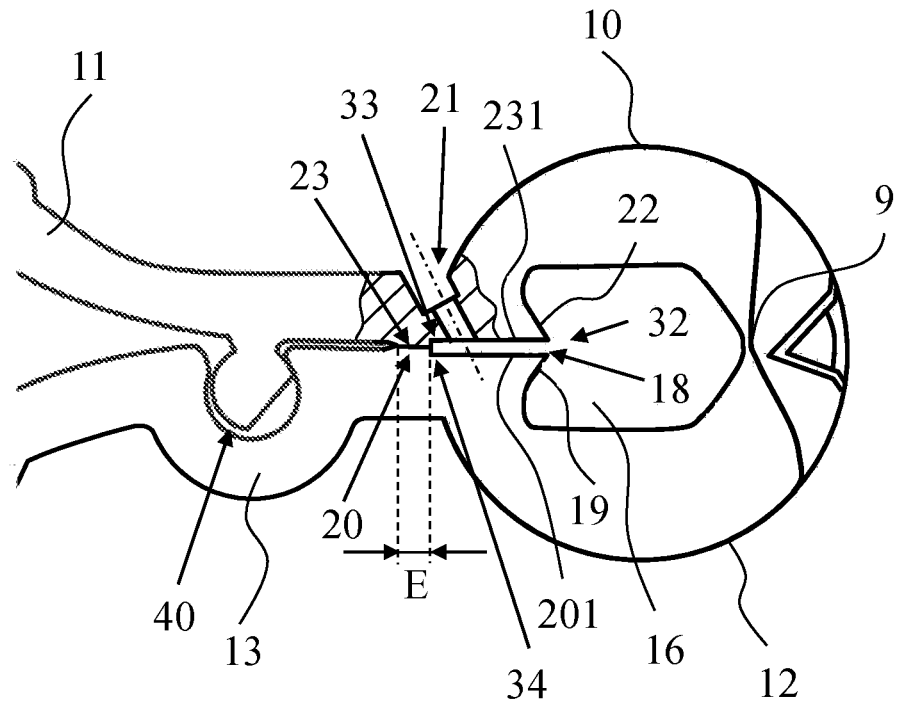
FIG. 18 shows a cross-sectional view of a fifth embodiment of a cartridge according to the invention in the closed state; and, FIG. 19 shows a perspective view of the cartridge according to FIG. 18 in the open state.

FIG. 18 illustrates a fifth embodiment according to the invention. The wing 11 is provided with a filling opening 21 which is suitable for receiving the injection needle 25. The filling opening 21 leads out at a surface 231 of the rib 22, which is set back in the direction of the receiving space 16 compared with the surface 23 of the rib. Between the surface 23 and the surface 231, there is thus a falling step 33, which extends along the entire length of the rib 22. In the closed state of the cartridge 6, the surface 23 comes into contact with the surface 20 of the wing 13.

Preferably, the surface 20 is likewise set back in the direction of the receiving space 16, thereby forming a surface 201 which extends along the entire length of the rib 19. A falling step 34 is thus formed between the surface 201 and the surface 20. The contact plane between the surface 20 and the surface 23 preferably forms a plane of symmetry with respect to the set-back surfaces 201 and 231, such that the respective heights of the steps 33 and 34 have the same magnitude.

The area between the set-back surface 231 and the surface 20 or between the set-back surface 231 and the set-back surface 201 produces a clearance 32 which forms a feed duct 18 or a feed opening for the lubricant along the entire length of the ribs 19 and 22. The lubricant can thus penetrate into the receiving space 16 in a very widely distributed manner. In this way, it is possible to distribute a relatively large amount of lubricant very quickly into the receiving space 16.

The faces 20 and 23 have to be in contact in the closed state of the cartridge 6 such that a liquid-tight closure is ensured with respect to the lubricant introduced by means of the filling opening 21. In the embodiment illustrated in FIG. 18, the faces 20 and 23 are in contact over a width E. However, it is also possible for the width to be embodied in a larger manner and to reach as far as the snap connection 40 of the wings 11 and 13.

Figure 19:
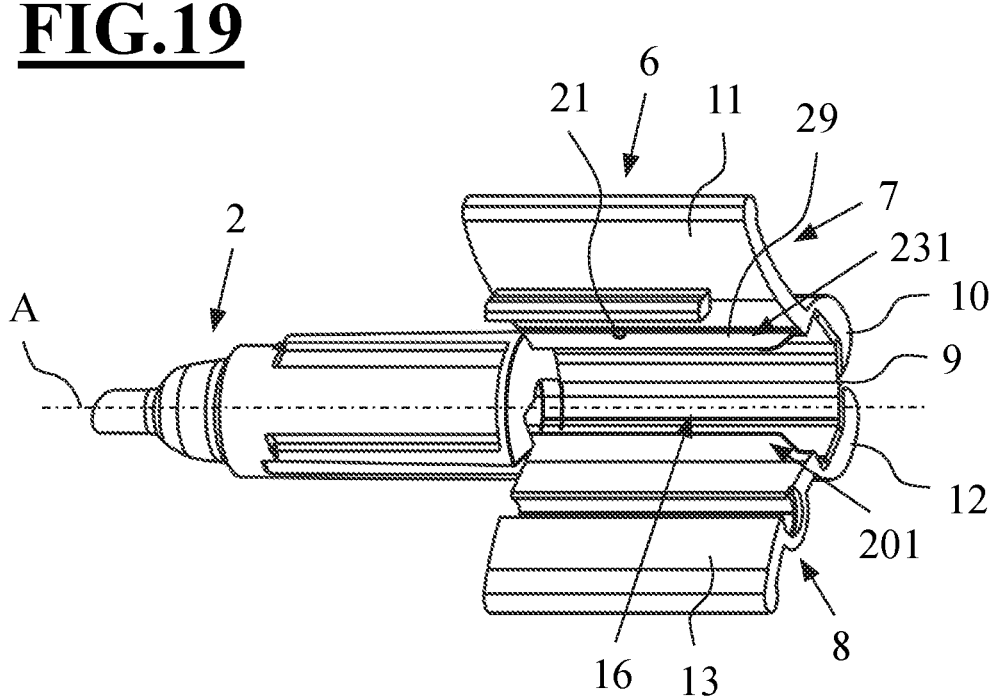

FIG. 19 illustrates a perspective illustration of the configuration of the cartridge 6 according to FIG. 18 in the open state.

It is understood that the foregoing description is that of the preferred embodiments of the invention and that various changes and modifications may be made thereto without departing from the spirit and scope of the invention as defined in the appended claims.

What is claimed is:

1. A cartridge for accommodating an intraocular lens, the cartridge defining a longitudinal axis (A) and comprising:
    first and second cartridge parts pivotally moveable relative to each other about said longitudinal axis (A) to define an open state and a closed state;
    said first cartridge part having a gutter-shaped first base element and a first plate-like wing extending from said first base element;
    said second cartridge part having a gutter-shaped second base element and a second plate-like wing extending from said second base element;
    said first and second base elements conjointly defining at least a portion of a receiving chamber for said intraocular lens when said first and second cartridge parts are in said closed state;

a lubricant feed arrangement for supplying a lubricant for said intraocular lens into said receiving chamber from outside of said cartridge when said cartridge is in said closed state;

said lubricant feed arrangement including a first feed channel formed in one of said first and second cartridge parts and configured to open into said receiving chamber;

said one of said first and second cartridge parts having a rib formed therein so as to extend into said receiving chamber; and, said first feed channel being formed in said rib; and, wherein said receiving chamber having a predetermined length; and, said rib extends parallel to said longitudinal axis (A) and extends linearly over half of said predetermined length of said receiving chamber viewed in the direction of said longitudinal axis (A); and, wherein said rib has an upper side facing toward the other one of said first and second cartridge parts; and, said first feed channel is formed in said rib so as to have a gutter-like configuration and to be open toward said upper side.

2. The cartridge of claim 1, wherein said first feed channel is configured to be linear.

3. The cartridge of claim 1, said rib having a wedge-shaped configuration and said one of said first and second cartridge parts having a base and a wing extending from said base; and/or said base and said wing conjointly defining a transition zone therebetween; said transition zone having an inner side; and, said rib is configured at said inner side of said transition zone.

4. The cartridge of claim 3, wherein said rib is a first rib and the other one of said cartridge parts has a second rib formed therein so as to extend into said receiving chamber; said lubricant feed arrangement includes a second feed channel formed in said second rib; and, said first and second feed channels are arranged so as to be congruent and cover one another when said cartridge is in said closed state.

5. The cartridge of claim 4, wherein said first feed channel is orientated to said longitudinal axis (A) at an angle lying in a range of 60° to 120°.

6. The cartridge of claim 4, wherein each of said cartridge parts has a base and a wing extending from said base; and, said first feed channel is configured to be linear and has an end facing away from said receiving chamber and said end opening to the outside at the wing of one of said first and second cartridge parts when said cartridge is in said closed state.

7. A cartridge for accommodating an intraocular lens, the cartridge defining a longitudinal axis (A) and comprising:

first and second cartridge parts pivotally moveable relative to each other about said longitudinal axis (A) to define an open state and a closed state;

said first cartridge part having a gutter-shaped first base element and a first plate-like wing extending from said first base element;

said second cartridge part having a gutter-shaped second base element and a second plate-like wing extending from said second base element;

said first and second base elements conjointly defining at least a portion of a receiving chamber for said intraocular lens when said first and second cartridge parts are in said closed state;

a lubricant feed arrangement for supplying a lubricant for said intraocular lens into said receiving chamber from outside of said cartridge when said cartridge is in said closed state;

said lubricant feed arrangement including a first feed channel formed in one of said first and second cartridge parts and configured to open into said receiving chamber; and, said one of said first and second cartridge parts having a continuous fill hole formed therein so as to open into said first feed channel in said closed state of said cartridge and to open to the outside when said cartridge is in said closed state; and, said one of said first and second cartridge parts having a rib formed therein so as to extend into said receiving chamber; and, said first feed channel being formed in said rib; and, wherein said receiving chamber having a predetermined length; and, said rib extends parallel to said longitudinal axis (A) and extends linearly over half of said predetermined length of said receiving chamber viewed in the direction of said longitudinal axis (A); and, wherein said rib has an upper side facing toward the other one of said first and second cartridge parts; and, said first feed channel is formed in said rib so as to have a gutter-like configuration and to be open toward said upper side.

8. The cartridge of claim 7, wherein said first feed channel is orientated to said longitudinal axis (A) at an angle lying in a range of 60° to 120°.

9. The cartridge of claim 7, wherein each of said cartridge parts has a base and a wing extending from said base; and, said first feed channel is configured to be linear and has an end facing away from said receiving chamber and said end opening to the outside at the wing of one of said first and second cartridge parts when said cartridge is in said closed state.

10. An injector for introducing an intraocular lens into an eye, the injector comprising:

a cartridge for accommodating said intraocular lens and said cartridge defining a longitudinal axis (A); and, the cartridge including:

first and second cartridge parts pivotally moveable relative to each other about said longitudinal axis (A) to define an open state and a closed state;

said first cartridge part having a gutter-shaped first base element and a first plate-like wing extending from said first base element;

said second cartridge part having a gutter-shaped second base element and a second plate-like wing extending from said second base element;

said first and second base elements conjointly defining at least a portion of a receiving chamber for said intraocular lens when said first and second cartridge parts are in said closed state;

a lubricant feed arrangement for supplying a lubricant for said intraocular lens into said receiving chamber from outside of said cartridge when said cartridge is in said closed state;

said lubricant feed arrangement including a first feed channel formed in one of said first and second cartridge parts and configured to open into said receiving chamber;

said one cartridge part having a rib formed therein so as to extend into said receiving chamber; and, said first feed channel being formed in said rib.

* * * * *

UNITED STATES PATENT AND TRADEMARK OFFICE
CERTIFICATE OF CORRECTION

PATENT NO. : 10,675,148 B2  
APPLICATION NO. : 15/996273  
DATED : June 9, 2020  
INVENTOR(S) : Marco Mueller Page 1 of 1

It is certified that error appears in the above-identified patent and that said Letters Patent is hereby corrected as shown below:

Page 2:
(56) References Cited: delete "Dockhorn et al." and substitute -- Dockhom et al. -- therefor.

In Column 11:
Line 40: delete "a to" and substitute -- α to --
Line 41: delete "a" and substitute -- α -- therefor.

In Column 12:
Line 25: delete "a" and substitute -- α -- therefor.

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*